(12) United States Patent
Han

(10) Patent No.: US 12,138,562 B2
(45) Date of Patent: Nov. 12, 2024

(54) METHOD FOR PREPARING KAFFIR LIME EXTRACT AND COMPOSITION COMPRISING KAFFIR LIME EXTRACT

(71) Applicant: KOREA BIO INDUSTRIAL DEVELOPMENT, INC., Daegu (KR)

(72) Inventor: Hyun Je Han, Seoul (KR)

(73) Assignee: KOREA BIO INDUSTRIAL DEVELOPMENT, INC., Daegu (KR)

( * ) Notice: Subject to any disclaimer, the term of this patent is extended or adjusted under 35 U.S.C. 154(b) by 467 days.

(21) Appl. No.: 17/608,041

(22) PCT Filed: Jul. 31, 2020

(86) PCT No.: PCT/KR2020/010109
§ 371 (c)(1),
(2) Date: Nov. 1, 2021

(87) PCT Pub. No.: WO2021/025380
PCT Pub. Date: Feb. 11, 2021

(65) Prior Publication Data
US 2022/0212122 A1    Jul. 7, 2022

(30) Foreign Application Priority Data
Aug. 2, 2019    (KR) ........................ 10-2019-0094309

(51) Int. Cl.
*B01D 11/02*    (2006.01)
*A61L 9/013*    (2006.01)
(Continued)

(52) U.S. Cl.
CPC .......... *B01D 11/0288* (2013.01); *A61L 9/013* (2013.01); *C11D 1/146* (2013.01);
(Continued)

(58) Field of Classification Search
CPC .......... A61K 8/97; A61L 9/013; B01D 11/02; B01D 11/0284; B01D 11/0288;
(Continued)

(56) References Cited

U.S. PATENT DOCUMENTS

2018/0305825 A1* 10/2018 Alkhaldi ................ C23F 11/04

FOREIGN PATENT DOCUMENTS

JP    2010-094506 A    4/2010
KR    100780087 B1    11/2007
(Continued)

OTHER PUBLICATIONS

Nov. 24, 2020 International Search Report issued in International Patent Application No. PCT/KR2020/010109.
(Continued)

*Primary Examiner* — Patrick Orme
(74) *Attorney, Agent, or Firm* — Oliff PLC

(57) ABSTRACT

The present invention relates to a method for preparing a kaffir lime extract and compositions containing a kaffir lime extract. Specifically, the present invention relates to a deodorizing composition, a cleaning composition, a composition for removing scale, and a composition for removing green algae, which each contain the kaffir lime extract obtained by the method according to the present invention. The kaffir lime extract according to the present invention has an excellent deodorizing effect, cleaning effect, scale removing effect and green algae removing effect.

6 Claims, 3 Drawing Sheets

(51) Int. Cl.
*C11D 1/14* (2006.01)
*C11D 3/20* (2006.01)
*C11D 3/37* (2006.01)
*C11D 3/382* (2006.01)

(52) U.S. Cl.
CPC .......... *C11D 3/2065* (2013.01); *C11D 3/3749* (2013.01); *C11D 3/382* (2013.01)

(58) Field of Classification Search
CPC ........... C11D 1/146; C11D 1/29; C11D 1/722; C11D 1/83; C11D 3/2065; C11D 3/3707; C11D 3/3749; C11D 3/382
See application file for complete search history.

(56) References Cited

FOREIGN PATENT DOCUMENTS

| KR | 10-2014-0146313 A | 12/2014 |
| KR | 10-2015-0043694 A | 4/2015 |
| KR | 10-2016-0007336 A | 1/2016 |
| KR | 102109811 B1 | 5/2020 |

OTHER PUBLICATIONS

Karthikeyan Venkatachalam. "Changes in Phytochemicals and Antioxidant Properties of Kaffir Lime Leaves Under Chilling Storage". Khon Kaen Agr. J., Feb. 2019, vol. 47, appendix 1, pp. 531-536.
Feb. 19, 2020 Office Action issued in Korean Patent Application No. 10-2019-0094309.

* cited by examiner

METHOD FOR PREPARING KAFFIR LIME EXTRACT AND COMPOSITION COMPRISING KAFFIR LIME EXTRACT

TECHNICAL FIELD

The present invention relates to a method for preparing a kaffir lime extract and compositions containing a kaffir lime extract. Specifically, the present invention relates to a deodorizing composition, a cleaning composition, and a composition for removing scale or green algae, which each contain the kaffir lime extract obtained by the method according to the present invention. The kaffir lime extract according to the present invention has an excellent deodorizing effect, cleaning effect, scale removing effect and green algae removing effect.

BACKGROUND ART

A conventional deodorizing or cleaning composition contains various chemical components such as disinfectants, fragrances and synthetic polymers. However, these chemical components are harmful to the human body and may cause unpredictable side effects. In order to solve these problems, studies have been conducted on deodorizing agents or cleaning agents using various natural products.

Korean Patent Application Publication No. 2016-0007336 discloses a deodorant composition containing a highly branched cyclodextrin and a plant extract. In the composition disclosed in the above patent document, a plant extract obtained by extraction with a solvent such as water or ethanol from one or more plants selected from the group consisting of green tea, persimmon leave, citrus peel, and *Illicium verum* is contained as a component exhibiting a deodorizing effect.

Korean Patent Application Publication No. 10-0780087 discloses an environmentally friendly deodorant using hardwood vinegar and natural plant materials. The above patent document discloses a deodorant containing a plant solution prepared by steaming and aging plums, persimmon leaves, green tea leaves, ginkgo leaves, pine needles, lemons, and the like.

Although various natural substances exhibiting a deodorizing effect and a cleaning effect are known, the present invention is intended to provide a method for extracting an active ingredient having an excellent deodorizing effect and a cleaning effect from a natural product.

DISCLOSURE

Technical Problem

An object of the present invention is to provide a method for preparing a kaffir lime extract, which contains large amounts of components having excellent deodorizing, sterilizing and cleaning effects, from kaffir lime leaves. In addition, the present invention is intended to provide a deodorizing composition, a cleaning composition, and a composition for removing scale or green algae, which each contain the kaffir lime extract.

Technical Solution

The above object is accomplished by a method for preparing a kaffir lime extract, the method comprising steps of: low-temperature-treating kaffir lime leaves; washing the low-temperature-treated kaffir lime, followed by cutting into a size of 2 cm or less in width and 10 cm or less in length; freezing the cut kaffir lime leaves; adding purified water to the frozen kaffir lime leaves in an amount 5 to 10 times the weight of the kaffir lime leaves, followed by crushing and then heating at a temperature of 88° C. to 92° C. for 5 to 7 hours; and naturally cooling the heated and crushed materials to room temperature of 20° C. to 25° C., followed by filtration and concentration under reduced pressure.

Preferably, the step of low-temperature-treating the kaffir lime leaves comprises illuminating the kaffir lime leaves with an illuminance of 1,000 to 1,200 Lux for 9 hours/day to 11 hours/day at a temperature of 5° C. to 10° C. for 8 to 12 days.

Preferably, the freezing comprises allowing the cut kaffir lime leaves to stand at a temperature of −10° C. to −5° C. for 20 hours to 30 hours.

Preferably, the time to reach the freezing temperature from room temperature may be 4 to 6 hours.

Preferably, the method further comprises, after the concentration under reduced pressure, a step of cold-storing the concentrate at a temperature of 2° C. to 6° C. for 24 hours or more, followed by separation into a supernatant and a pellet fraction and storage.

In addition, the above object is accomplished by: a deodorizing composition containing, based on the total weight of the composition, 10 wt % to 20 wt % of a supernatant of the kaffir lime extract; a washing composition containing, based on the total weight of the composition, 20 wt % to 40 wt % of a pellet fraction of the kaffir lime extract; a composition for removing scale containing, based on the total weight of the composition, 20 wt % to 40 wt % of a pellet fraction of the kaffir lime extract, 1 wt % to 5 wt % of a *papaya* extract, 1 wt % to 5 wt % of polypropylene glycol, and 1 to 10 wt % of $C_{10\text{-}16}$ ethoxylated propoxylated alcohol; and a composition for removing green algae containing, based on the total weight of the composition, 20 wt % to 40 wt % of a pellet fraction of the kaffir lime extract, 1 to 5 wt % of sodium lauryl ether sulfate, 1 to 5 wt % of polypropylene glycol, and 1 to 10 wt % of $C_{10\text{-}16}$ ethoxylated propoxylated alcohol.

Advantageous Effects

The extraction method according to the present invention may effectively extract components having excellent deodorizing and cleaning effects from kaffir lime leaves. In addition, the composition containing the kaffir lime extract obtained by the extraction method of the present invention has an excellent deodorizing effect, cleaning effect, scale removing effect and green algae removing effect.

MODE FOR INVENTION

Unless otherwise defined, all technical terms used in the present invention have the following definitions and have the meanings as commonly understood by those skilled in the art to which the present invention pertains. In addition, although preferred methods or samples are described herein, those similar or equivalent thereto are included within the scope of the invention.

The term "about" means the amount, level, value, number, frequency, percent, dimension, size, quantity, weight or length which changes by 30, 25, 20, 15, 10, 9, 8, 7, 6, 5, 4, 3, 2 or 1% relative to the referred amount, level, value, number, frequency, percent, dimension, size, quantity, weight or length.

Throughout the present specification, the terms "comprises" and "comprising", when not explicitly required in the context, include a stated step or element, or group of steps or elements, but it should be understood that any other step or element, or group of steps or elements, is not excluded.

Hereinafter, the present invention will be described in more detail with reference to the accompanying drawings.

Figure 1:
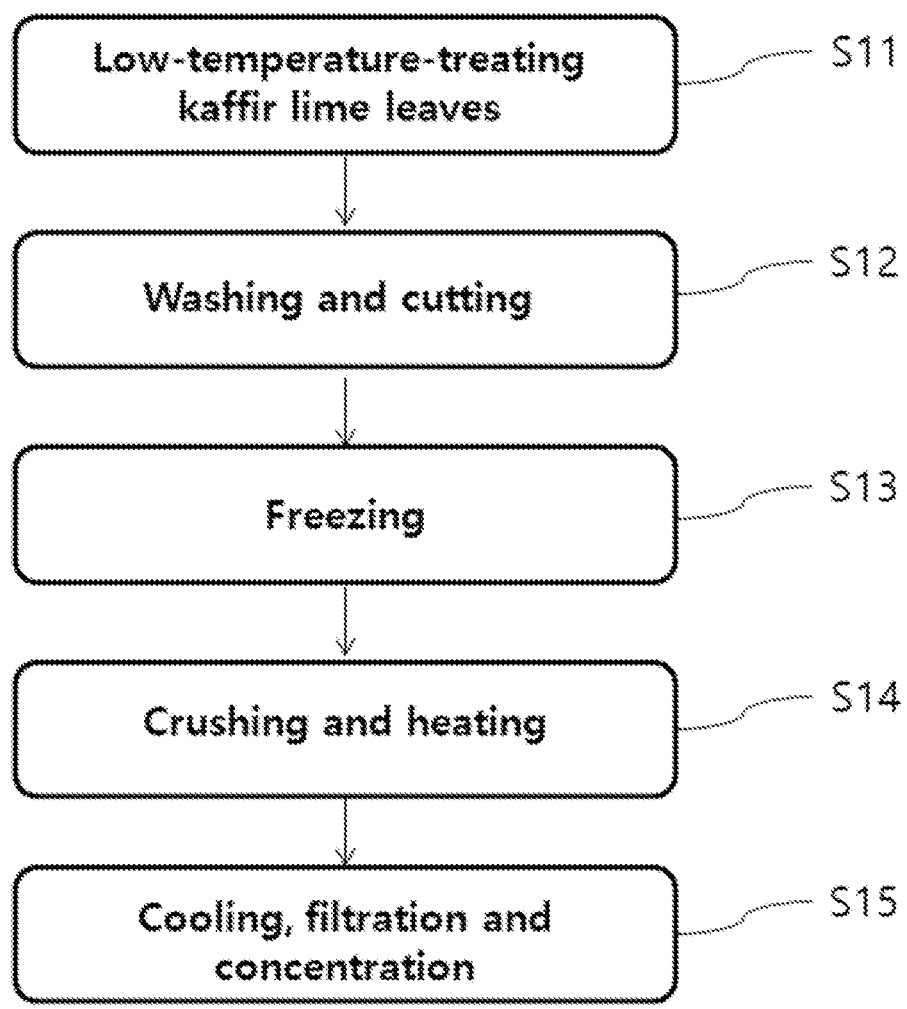
FIG. 1 schematically shows a method for preparing a kaffir lime extract according to the present invention.

FIG. 1 schematically shows a method for preparing a kaffir lime extract according to the present invention.

The method for preparing a kaffir lime extract according to the present invention comprises steps of: (S11) low-temperature-treating kaffir lime leaves; (S12) washing the low-temperature-treated kaffir lime, followed by cutting into a size of 2 cm or less in width and 10 cm or less in length; (S13) freezing the cut kaffir lime leaves; (S14) adding purified water to the frozen kaffir lime leaves in an amount 5 to 10 times the weight of the kaffir lime leaves, followed by crushing and then heating at a temperature of 88° C. to 92° C. for 5 to 7 hours; and (S15) naturally cooling the heated and crushed materials to room temperature of 20° C. to 25° C., followed by filtration and concentration under reduced pressure.

Hereinafter, each step will be described in detail.

First, kaffir lime leaves are subjected to low-temperature treatment (S11). Kaffir lime (*Citrus hystrix*) is a plant belonging to *Citrus* of Rutaceae and is a type of lime. It is known that the fruit of kaffir lime is rarely eaten and the leaves thereof are mainly used. Kaffir lime leaves are mainly used as a spice for food in Southeast Asia. In the present invention, kaffir lime leaves collected in nature are used.

In the low-temperature treatment step (S11), the kaffir lime leaves are preferably treated at a temperature of 5° C. to 10° C. for 8 to 12 days. According to one embodiment of the present invention, the step of low-temperature-treating the kaffir lime leaves comprises illuminating the kaffir lime leaves with an illuminance of 1,000 to 1,200 Lux for 9 hours/day to 11 hours/day. In particular, the leaves may be changed to the maple leaf color by controlling temperature, time and illumination conditions. As the leaves are changed to the maple leaf color, the effects of changing the physiologically active substances in plant cells and increasing the contents thereof can be expected. In fact, the extract obtained by the extraction method comprising the low-temperature treatment step has a better deodorizing effect, cleaning effect, scale removing effect and green algae removing effect than an extract obtained without the low-temperature treatment.

Next, the low-temperature-treated kaffir lime leaves are washed and cut (S12). The low-temperature-treated kaffir lime leaves are washed to remove impurities, and cut into a size of 2 cm or less in width and 10 cm or less in length.

Subsequently, the cut kaffir lime leaves are frozen (S13).

The freezing is preferably performed by slowly cooling the cut kaffir lime leaves from room temperature to a temperature of −10° C. to −5° C. over 4 hours to 6 hours, followed by allowing to stand at a temperature of −10° C. to −5° C. for 20 to 30 hours. As the freezing treatment is performed after the cutting, the plant tissue and cell walls may be destroyed by freezing of moisture in the plant cells, so that active ingredients may be more easily extracted. In addition, the freezing treatment also has an effect of preventing changes in intracellular components and decay thereof. The time to reach the freezing temperature from the room temperature is preferably about 4 to 6 hours. Since rapid cooling may modify the active ingredients, slow cooling is preferred.

Purified water is added to the frozen kaffir lime leaves in an amount 5 to 10 times the weight of the kaffir lime leaves, and the kaffir lime leaves are crushed and then heated at a temperature of 88° C. to 92° C. for 5 to 7 hours (S14). The purified water added during the crushing preferably has a temperature of 10° C. or lower. Since the frozen leaves are crushed, it is preferable to use low-temperature water at 10° C. or lower if possible. A conventional crushing machine may be used for the crushing, and there is no particular limitation thereon.

After the leaves are crushed to have a small particle size, active ingredients are extracted by heating the crushed materials to a temperature of 88° C. to 92° C. without a separate filtration process. Preferably, the crushed product is heated for 5 to 7 hours.

Finally, the heated crushed materials is cooled naturally to room temperature of 20° C. to 25° C., and then filtered and concentrated under reduced pressure (S15). The filtration is performed using a conventional pre-filter, and the residue is removed. Then, the first filtrate is filtered under reduced pressure filtration using a fine filter (pore size: 1 μm or less), thereby extracting water-soluble active ingredients. The extract may be concentrated to 1/10 of the initial weight by means of a concentrator for food.

According to one embodiment of the present invention, the method further comprises a step of cold-storing the filtered and concentrated extract until the extract is separated into a supernatant and a pellet fraction, and storing the supernatant and the pellet fraction separately. The cold storage may be performed using a plastic container, and after 24 hours of storage, the extract is separated into a supernatant and a pellet fraction. At this time, the supernatant and the pellet fraction may be stored separately and used according to the intended use.

The kaffir lime extract prepared according to the present invention has an excellent deodorizing effect, cleaning effect, scale removing effect and green algae removing effect.

According to one embodiment of the present invention, there is provided a deodorizing composition containing the kaffir lime extract. The deodorizing composition is characterized by containing, based on the total weight of the composition, 10 to 20 wt % of a supernatant of the kaffir lime extract. The deodorizing composition may contain the supernatant and the balance of purified water. The deodorizing composition may contain the supernatant having a relatively small content of the kaffir lime extract.

According to an embodiment of the present invention, the deodorizing composition of the present invention may be used as an air deodorant, a fiber deodorant, or the like.

According to one embodiment of the present invention, there is provided a cleaning composition containing the kaffir lime extract. The cleaning composition is characterized by containing, based on the total weight of the composition, 20 to 40 wt % of a pellet fraction of the kaffir lime extract. The cleaning composition may contain the pellet fraction and the balance of purified water. In order to increase the cleaning effect thereof, the cleaning composition preferably contains a pellet fraction of the kaffir lime extract, which has a relatively high content of the extract, and it may further contain a *papaya* extract, preferably *papaya* oil. According to one embodiment of the present invention, the cleaning composition contains, based on the total weight of the composition, 10 wt % to 40 wt % of a pellet fraction of the kaffir lime extract, 1 wt % to 5 wt % of *papaya* oil, and the balance of purified water. The cleaning composition may be used as a cosmetic composition such as soap, shampoo, cleansing, or body shampoo, and may also be used as a laundry detergent, an industrial detergent, or the like. In particular, the cleaning composition according to the present invention exhibits an excellent cleaning effect without affecting the intrinsic properties of the object to be cleaned.

According to one embodiment of the present invention, there is provided a composition for removing scale containing the kaffir lime extract. The composition for removing scale is characterized by containing, based on the total weight of the composition, 20 wt % to 40 wt % of a pellet fraction of the kaffir lime extract, 1 wt % to 5 wt % of a *papaya* extract, 1 wt % to 5 wt % of polypropylene glycol, and 1 to 10 wt % of $C_{10-16}$ ethoxylated propoxylated alcohol.

The composition for removing scale according to the present invention can effectively remove scale formed on equipment for cooling water such as cooling towers, freezers, or water-cooled air conditioners, and hot water equipment such as boilers. The composition is an alkaline aqueous solution. The composition according to the present invention can inhibit the formation of total dissolved solids (TDS), which are a precursor of scale, through the breakage of molecular bonds by the kaffir lime extract that penetrated between insoluble salts and foreign substances (scum), which are scale-forming materials. In addition, the kaffir lime extract can penetrate the already formed scale and break the surface molecular bond between the equipment surface and the scale materials deposited thereon, thereby completely removing the scale without damage to the equipment. In particular, the composition for removing scale according to the present invention can function to remove scale and suppress scale formation even during equipment operation, and exhibit a sufficient effect even when it is added in small amounts.

According to one embodiment of the present invention, there is provided a composition for removing green algae containing the kaffir lime extract. The composition for removing green algae may contain, based on the total weight of the composition, 20 wt % to 40 wt % of a pellet fraction of the kaffir lime extract, 1 to 5 wt % of sodium lauryl ether sulfate, 1 to 5 wt % of polypropylene glycol, and 1 to 10 wt % of $C_{10}$-$C_{16}$ ethoxylated propoxylated alcohol. A method for removing green algae using the composition of the present invention is as follows. First, after green alga are removed by a physical method, the composition for removing green algae may be sprayed at a concentration of 1/1,000 to 1/10,000 of the total volume of a green algae-generated water system, once every 3 days for the first 15 days, and then once every 7 days after days 15, thereby removing green algae.

Hereinafter, the present invention will be described in detail with reference to examples. However, the scope of the present invention is not limited by these examples.

Example 1

1 kg of kaffir lime leaves were prepared and subjected to low-temperature treatment at a temperature of 5 to 10° C. for 10 days. In the low-temperature treatment, the kaffir lime leaves were illuminated with an illuminance of 1,000 to 1,200 Lux for 10 hours/day. After 10 days, the low-temperature-treated leaves were washed by watering, and impurities other than the leaves were removed. The washed leaves were cut into a size of 2 cm or less in width and 10 cm or less in length, and the cut kaffir lime leaves were cooled slowly from room temperature to −10° C. over 6 hours, and then frozen at a temperature of −10° C. for 24 hours. The frozen leaves were mixed with a 5-fold weight of purified water (10° C. or lowers), crushed with a grinder, and then heated at 90° C. for 6 hours. Next, the crushed materials was cooled naturally to room temperature, filtered through a pre-filter, and the filtered through a fine filter (pore size: 1 μm) under reduced pressure. The resulting extract was concentrated to 1/10 of the initial weight thereof, and cold-stored for 24 hours until it was separated into an upper layer (supernatant) and a lower layer (pellet fraction), thus obtaining a kaffir lime extract of the upper layer and a kaffir lime extract of the lower layer.

Comparative Example 1

A kaffir lime extract of the upper layer and a kaffir lime extract of the lower layer were obtained in the same manner as in Example 1, except that the low-temperature treatment was not performed.

Comparative Example 2

A kaffir lime extract of the upper layer and a kaffir lime extract of the lower layer were obtained in the same manner as in Example 1, except that the low-temperature treatment and the freezing treatment were not performed.

Comparative Example 3

1 kg of kaffir lime leaves were prepared and washed by watering to remove impurities other than the leaves. The washed leaves were dried and then cut into a size of 2 cm or less in width and 10 cm or less in length. The cut leaves were extracted under reflux with a 70% (v/v) ethanol aqueous solution three times for 5 hours each time, and then subjected to cold extraction. Then, the extract was filtered through a pre-filter, filtered through a fine filter (pore size: 1 μm) under reduced pressure, and concentrated, thus obtaining an ethanol extract of kaffir lime. The extract was dissolved in purified water to a concentration of 10% (v/v) and used in the following experiment.

Experimental Example 1: Deodorizing Effect 20 ml of each of the supernatant of the kaffir lime extract obtained in Example 1, the supernatant of the kaffir lime extract obtained in each of Comparative Examples 1 and 2, and the solvent extract of kaffir lime obtained in Comparative Example 3 was prepared, and 20 ml of purified water was prepared as a control. Each prepared sample was placed and sealed in a 5-L reactor, and then ammonia ($NH_3$), trimethylamine (($CH_3$)N) and hydrogen sulfide ($H_2S$) were added thereto at concentrations of 50 ppm and the time-dependent concentrations thereof were measured. The concentrations of the test gases were measured according to KS 2218:2009. During the test, the temperature was maintained at 23° C.±5° C., and the relative humidity was maintained at 50%±10%. The removal rate (deodorization rate) of each test gas was calculated by [{(control concentration)−(sample concentration)}/(control concentration)]×100. The results of the measurement are shown in Tables 1 to 3 below.

Figure 3:
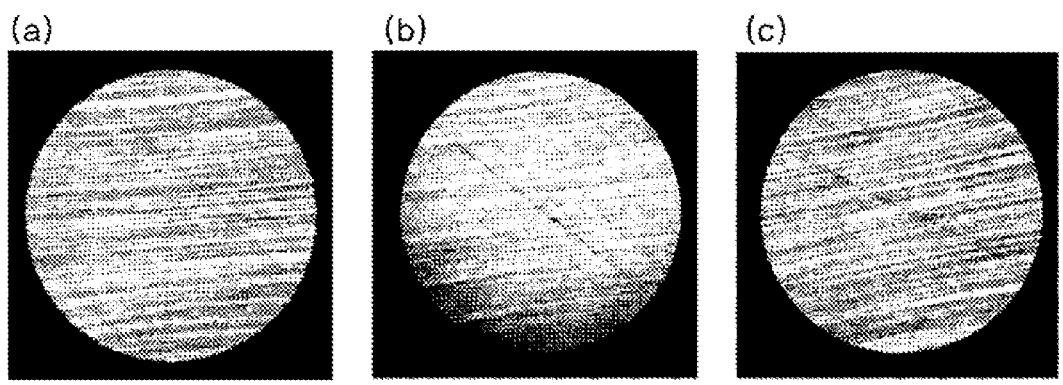
FIG. 3 depicts photograph showing the cleaning effect of a cleaning composition, which contains a kaffir lime extract prepared according to the present invention, on an aluminum disk.

In addition, the cleaning composition was diluted at a ratio of 1:00 with purified water, heated to a temperature of 50° C., and then immersed for 16 hours in an industrial aluminum disk subjected to post-processing (protective oil film treatment). This process was repeated five times. As a control, a 5% NaOH solution, which is conventionally used, was immersed for 16 seconds in an industrial aluminum disc subjected to post-processing (protective oil film treatment). FIG. 3 shows photographs of the aluminum disks after the cleaning process.

FIG. 3(a) is a photograph of the surface of an aluminum disk surface before cleaning after post-processing, FIG. 3(b) is a photograph of the aluminum disk surface cleaned with the control (NaOH) solution, and FIG. 3(c) is a photograph of the aluminum disk surface cleaned with the cleaning composition of the present invention. Referring to FIG. 3, it can be confirmed that, in the case of the control (FIG. 3b)), the oil film was removed, but the intrinsic texture of the aluminum disc was damaged, in the case of the cleaning composition of the present invention (FIG. 3c), the oil film was removed clean and the intrinsic texture of the aluminum disk was also not damaged (no surface corrosion).

TABLE 1

| Elapsed time (min) | Ammonia ($NH_3$) concentration (ppm)/deodorization rate (%) | | | | | | | |
|---|---|---|---|---|---|---|---|---|
| | Control | | Example 1 | | Comparative Example 1 | | Comparative Example 2 | | Comparative Example 3 |
| 0 | 50 | | 50 | 0 | 50 | 0 | 50 | 0 | 50 | 0 |
| 30 | 49 | | 1 | 98.0 | 36 | 28 | 43 | 14 | 47 | 6 |
| 60 | 49 | | 0 | 100 | 33 | 34 | 40 | 20 | 45 | 10 |
| 90 | 48 | | 0 | 100 | 32 | 36 | 39 | 22 | 43 | 14 |
| 120 | 48 | | 0 | 100 | 31 | 38 | 39 | 22 | 42 | 16 |

TABLE 2

| Elapsed time (min) | Trimethylamine (($CH_3$)N) concentration (ppm)/deodorization rate (%) | | | | | | | |
|---|---|---|---|---|---|---|---|---|
| | Control | | Example 1 | | Comparative Example 1 | | Comparative Example 2 | | Comparative Example 3 |
| 0 | 50 | | 50 | 0 | 50 | 0 | 50 | 0 | 50 | 0 |
| 30 | 49 | | 2 | 96.0 | 40 | 20 | 45 | 10 | 48 | 4 |
| 60 | 49 | | 1 | 98.0 | 39 | 22 | 43 | 14 | 47 | 6 |
| 90 | 49 | | 0 | 100 | 39 | 22 | 43 | 14 | 46 | 8 |
| 120 | 48 | | 0 | 100 | 38 | 24 | 42 | 16 | 46 | 8 |

TABLE 3

| Elapsed time (min) | Hydrogen sulfide ($H_2S$) concentration (ppm)/deodorization rate (%) | | | | | | | |
|---|---|---|---|---|---|---|---|---|
| | Control | | Example 1 | | Comparative Example 1 | | Comparative Example 2 | | Comparative Example 3 |
| 0 | 50 | | 50 | 0 | 50 | 0 | 50 | 0 | 50 | 0 |
| 30 | 49 | | 3 | 93.9 | 38 | 24 | 44 | 12 | 48 | 4 |
| 60 | 48 | | 1 | 97.9 | 36 | 28 | 42 | 16 | 46 | 8 |
| 90 | 48 | | 0 | 100 | 35 | 30 | 41 | 18 | 46 | 18 |
| 120 | 48 | | 0 | 100 | 35 | 30 | 41 | 18 | 45 | 10 |

Figure 2:
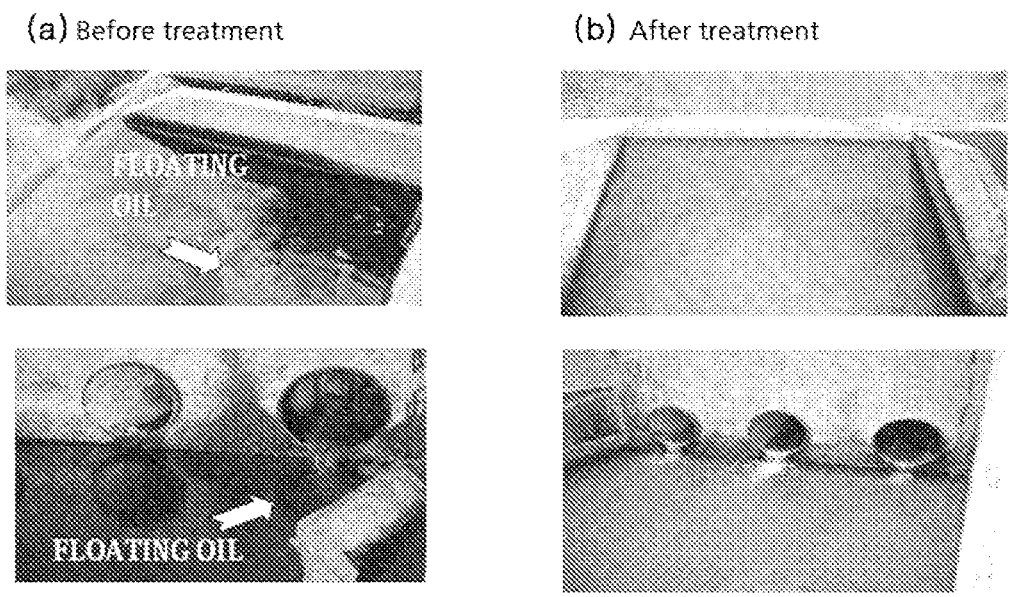
FIG. 2 depicts photograph showing the cleaning effect of a cleaning composition, which contains a kaffir lime extract prepared according to the present invention, on oil-contaminated water.

Experimental Example 2: Cleaning Effect 20 wt % of the pellet fraction of the kaffir lime extract prepared in Example 1, 3 wt % of a *papaya* extract and the balance of purified water were mixed together, thus preparing a cleaning composition. A river surface contaminated with oil was treated with the prepared cleaning composition 6 times at 4 hour intervals for 24 hours, and the surface before treatment and the surface after treatment were compared with each other. The results are shown in FIG. 2. Referring to FIG. 2, oil floating on the river surface was observed before treatment with the cleaning composition of the present invention, but the oil was not observed after the treatment was completed.

Experimental Example 3: Scale Removing Effect 30 wt % of the pellet fraction of the kaffir lime extract prepared in Example 1, 2.5 wt % of a *papaya* extract, 3 wt % of polypropylene glycol, 3 wt % of $C_{10-16}$ ethoxylated propoxylated alcohol, and the balance of purified water were mixed together, thus preparing a composition for removing scale.

Figure 4:
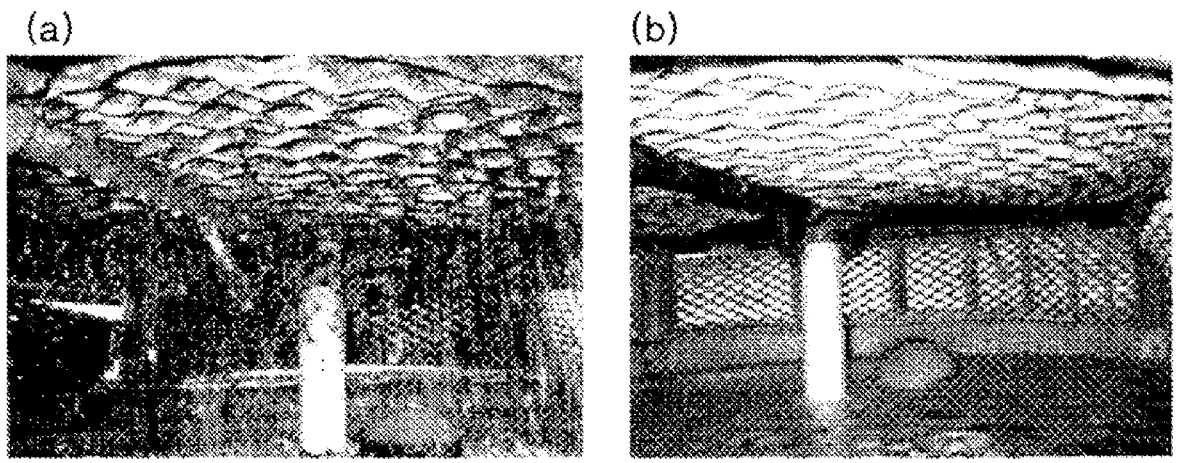
FIG. 4 depicts photograph showing the scale removing effect of a composition for removing scale, which contains a kaffir lime extract prepared according to the present invention, on a cooling tower.

The composition for removing scale was applied to a cooling tower. First, while the cooling tower was operated, the composition at a concentration of 1,000 ppm was introduced into the storage tank of the cooling tower once/week. After 2 weeks, the scale attached to the cooling tower started to detach, and after 4 weeks, the scale and impurities were peeled off and started to collect at the bottom. FIG. 4 shows photographs of the inside of the cooling tower before introduction of the composition (FIG. 4(a)) and after introduction of the composition (FIG. 4(b)).

Figure 5:
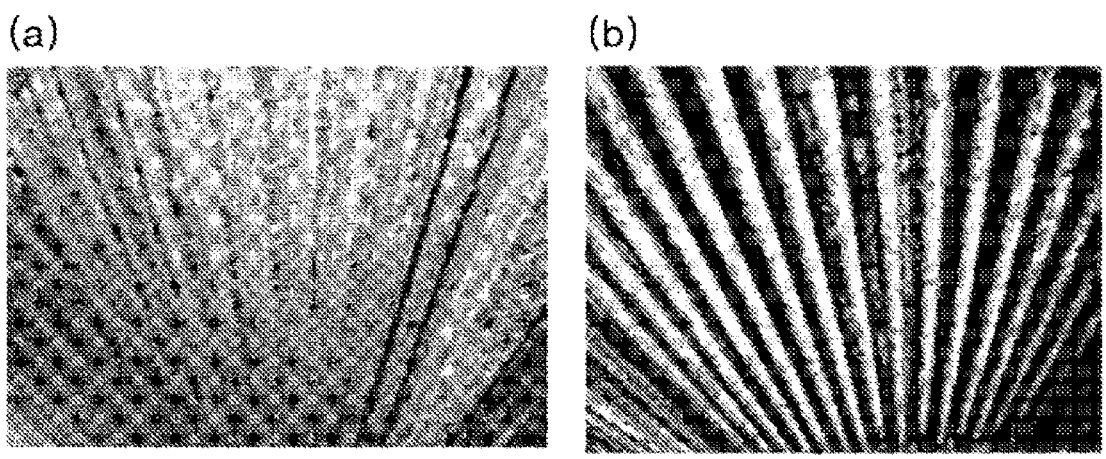
FIG. 5 depicts photograph showing the scale removing effect of a composition for removing scale, which contains a kaffir lime extract prepared according to the present invention, on an Eva-Con (evaporative condenser) pipe surface.

In addition, the composition for removing scale was applied to Eva-Con (evaporative condenser) pipes. The Eva-Con pipes were treated once a week with the composition at a concentration of 1,000 ppm. After 4 weeks, scale was removed from the Eva-Con pipe surface. FIG. 5 shows photographs of the Eva-Con pipe surfaces before introduction of the composition (FIG. 5(a)) and after introduction of the composition (FIG. 5(b)).

Experimental Example 4: Green Algae Removing Effect 38.5 wt % of the pellet fraction of the kaffir lime extract prepared in Example 1, 2.5 wt % of sodium lauryl ether sulfate, 3.0 wt % of polypropylene glycol, 3.0 wt % of $C_{10-16}$ ethoxylated propoxylated alcohol, and the balance of purified water were mixed together, thus preparing a composition for removing green algae.

Two freshwater samples, each having a volume of 1 L, were collected from the water hazards of Midas CC (Icheon, Gyeonggi-do, Korea), and green alga were removed from each sample by a physical method. Then, sample 1 was used as a control in an untreated state, and the composition for removing green algae was applied to sample 2 at a concentration of 1,000 ppm. After 120 hours, the water samples were analyzed. The analysis was carried out based on the water pollution process test standards (Ministry of Environment Notification No. 2014-164, Sep. 22, 2014). The results of the analysis are shown in Table 4 below.

fied water were mixed together, thus preparing a composition for removing green algae.

A freshwater green alga (Pseudokirchneriella subcapitata, ATTC No. 22662), which is widely used as an environmental and ecological toxicity test organism, was prepared and cultured in a freshwater green algae incubator (J-SCI, Jisico Co., Korea) under the following environmental conditions: a temperature of 21 to 24° C., 24 hours of illumination, an of illumination 4440 to 8880 Lux, and a speed of 100 rpm. The culture container used was a 250-mL Erlenmeyer flask made of glass for easy observation. The freshwater alga was subcultured at intervals of 4 weeks. As the culture medium, OECD-recommended medium (OECD TG 201, Annex 3 Growth media) was used.

The test concentrations were set to 100 mg/L, 1,000 mg/L, and 10,000 mg/L. To prepare test solutions for measuring the effect of removing green algae, 0.2 g, 2.0 g and 20 g of the prepared composition for removing green algae were weighed accurately and added to and thoroughly mixed with 2 L of OECD-recommended medium as test water in a volumetric flask, thus preparing test solutions (100 mg/L, 1,000 mg/L, and 10,000 mg/L). A negative control was the OECD-recommended medium which is test water.

After 7 days of pre-culture, the freshwater alga that reached the exponential growth stage was inoculated into each test container at a density of $1.0 \times 10^5$ cells/mL. The test container was a 2-L glass beaker.

For all the test containers, the number of cells per mL of test water was counted before treatment with the test substance and at 10 and 30 minutes after treatment with the test substance. The number of freshwater algae cells was counted under a microscope using a hemocytometer. The efficiency (%) of removal of the freshwater alga (Pseudokirchneriella subcapitata, ATTC No. 22662) was calculated as the difference between the initial algae cell concentration of algae and the algae cell concentration after treatment with the test substance. The results are shown in Table 5 below. In addition, during the test period, the pH of the test solution in each test container was measured using

TABLE 4

|  | COD | Suspended matter | pH | Turbidity | Total nitrogen | Total phosphorus |
|---|---|---|---|---|---|---|
| Sample 1 | 22.4 | 20.0 | 7.0 | 83.9 | 6.6 | 0.38 |
| Sample 2 | 12.2 | 14.0 | 4.3 | 10.8 | 4.0 | 0.10 |
| Increase or decrease rate | −45.5% | −30.0% | −38.6% | −87.1% | −39.4% | −73.7% |

Referring to Table 4 above, the sample treated with the green algae removal composition of the present invention showed a decrease in COD of 45.5%, a decrease in suspended matter of 30.0%, and also significant decreases in pH, turbidity, total nitrogen and total phosphorus, compared to the control sample 1, suggesting that the green algae removal composition of the present invention has an excellent effect of removing green algae based on its excellent water purification ability.

Example 5: Experiment on Green Algae Removing Effect 38.5 wt % of the pellet fraction of the kaffir lime extract prepared in Example 1, 2.5 wt % of sodium lauryl ether sulfate, 3.0 wt % of polypropylene glycol, 3.0 wt % of $C_{10-16}$ ethoxylated propoxylated alcohol, and the balance of puria pH meter (Orion 3 Star, Thermo Scientific Co., Ltd., USA) for the negative control group at the start of the test and the group treated with each concentration of the test substance. The results of the measurement are shown in Table 6 below.

TABLE 5

|  | After 10 minutes | | After 30 minutes | |
|---|---|---|---|---|
| Test concentration (mg/L) | Cell concentration (cells/mL) | Removal efficiency (%) | Cell concentration (cells/mL) | Removal efficiency (%) |
| 100 | 66,250 | 32.1 | 30,000 | 69.2 |
| 1,000 | 50,000 | 48.7 | 20,000 | 79.5 |
| 10,000 | 40,000 | 59.0 | 11,250 | 88.5 |

* Initial concentration: $0.975 \times 10^5$ cells/mL

TABLE 6

| Observation time | Test concentration | | | |
|---|---|---|---|---|
| | Control | 100 | 1,000 | 10,000 |
| 100 | 7.59 | 7.45 | 7.47 | 9.21 |

Referring to Tables 5 and 6 above, it can be seen that the composition for removing green algae according to the present invention removes the freshwater alga (Pseudokirchneriella *subcapitata*) with excellent efficiency.

Experimental Example 6: Toxicity Test

A *Daphnia magna* acute toxicity test was performed to examine whether or not the kaffir lime extract of the present invention is toxic. *Daphnia magna* is a species that is used as a test organism in an ecotoxicity test. *Daphnia magna* was bred in a 1-L cylindrical glass tank at a water temperature of 19 to 21° C. with a 16-hr light (08:00 to 24:00)/9-hr dark (24:00 to 08:00) cycle. As food, *Chlorella* sp. was supplied once in the morning. The culture medium used was a culture medium prepared in accordance with the "Acute toxicity test method for *Daphnia magna* (ES 04751.1) in Pollution Process Test Standards".

1 L (concentration: 1000 mg/L) of the supernatant of the kaffir lime extract prepared in Example 1 was aliquoted and fed at concentrations of 6.25%, 12.5%, 25%, 50% and 100% to a water tank containing *Daphnia magna*. The extract was not fed to a control group. For all the test water tanks, general intoxication symptoms, specific symptoms and immobilization were observed at 24 hours after the start of the test. For the determination of immobilization, observation was performed about 15 seconds after quiet movement of the test container, and individuals, which showed movement of some organs (tactile sense, hind abdomen, etc.) but were immobile, were regarded as immobile individuals. The results of measuring the number of immobile individuals and general symptoms of intoxication are shown in Table 7 below.

TABLE 7

| Concentration (%) | Number of Daphnia magna individuals | Number of immobile Daphnia magna individuals (24 hrs) | | Immobility (%) (24 hrs) | | Abnormal behavior (24 hrs) | |
|---|---|---|---|---|---|---|---|
| | | A | B | A | B | A | B |
| Control | 20 | 0 | 0 | 0 | 0 | NOR | NOR |
| 6.25 | 20 | 0 | 0 | 0 | 0 | NOR | NOR |
| 12.5 | 20 | 0 | 0 | 0 | 0 | NOR | NOR |
| 25 | 20 | 9 | 7 | 45 | 35 | LET(2) | SUR(2) |
| 50 | 20 | 19 | 18 | 95 | 90 | LET(1) | LET(2) |
| 100 | 20 | 20 | 20 | 100 | 100 | — | — |

A: abnormal behavior 10 minutes after sample treatment,
B: abnormal behavior 30 minutes after sample treatment;
Abbreviations;
NOR (Normal),
LET (Lethargized),
SUR (Daphnia mainly at the surface)

Numbers in parentheses: the number of *Daphnia magna* individuals

Referring to Table 7 above, it can be confirmed that, when the kaffir lime extract according to the present invention was fed at a concentration of 12.5% or lower, it had little effect on the survival of *Daphnia magna*.

The invention claimed is:

1. A method for preparing a kaffir lime extract, the method comprising steps of:
    low-temperature-treating kaffir lime leaves;
    washing the low-temperature-treated kaffir lime leaves, followed by cutting into a size of 2 cm or less in width and 10 cm or less in length;
    freezing the cut kaffir lime leaves;
    adding purified water to the frozen cut kaffir lime leaves in an amount 5 to 10 times the weight of the cut kaffir lime leaves, followed by crushing and then heating at a temperature of 88° C. to 92° C. for 5 to 7 hours; and
    cooling the heated and crushed materials to room temperature of 20° C. to 25° C., followed by filtration and concentration,
    wherein the step of low-temperature-treating the kaffir lime leaves comprises illuminating the kaffir lime leaves with an illuminance of 1,000 to 1,200 Lux for 9 hours/day to 11 hours/day at a temperature of 5° C. to 10° C. for 8 to 12 days.

2. The method of claim 1, wherein the freezing comprises allowing the cut kaffir lime leaves to stand at a temperature of −10° C. to −5° C. for 20 hours to 30 hours.

3. The method of claim 2, wherein the time to reach the freezing temperature from room temperature is 4 to 6 hours.

4. The method of claim 1, further comprising, after the concentration, a step of cold-storing the concentrate at a temperature of 2° C. to 6° C. for 24 hours or more, followed by separation into a supernatant and a pellet fraction and storage.

5. A composition for removing scale containing the pellet fraction of the kaffir lime extract obtained by the method of claim 4, the composition containing, based on the total weight of the composition, 20 wt % to 40 wt % of the pellet fraction of the kaffir lime extract, 1 wt % to 5 wt % of a *papaya* extract, 1 wt % to 5 wt % of polypropylene glycol, and 1 to 10 wt % of $C_{10-16}$ ethoxylated propoxylated alcohol.

6. A composition for removing green algae containing the pellet fraction of the kaffir lime extract obtained by the method of claim 4, the composition containing, based on the total weight of the composition, 20 wt % to 40 wt % of the pellet fraction of the kaffir lime extract, 1 to 5 wt % of sodium lauryl ether sulfate, 1 to 5 wt % of polypropylene glycol, and 1 to 10 wt % of $C_{10-16}$ ethoxylated propoxylated alcohol.

* * * * *